(12) United States Patent
Sananikone et al.

(10) Patent No.: US 12,161,746 B2
(45) Date of Patent: Dec. 10, 2024

(54) AEROSOL HAIR DYEING DEVICE BASED ON A CROTONIC ACID COPOLYMER AND A FATTY AMINE

(71) Applicant: L'OREAL, Paris (FR)

(72) Inventors: Malayphone Sananikone, Saint-Ouen (FR); David Seneca, Saint-Ouen (FR)

(73) Assignee: L'OREAL, Paris (FR)

( * ) Notice: Subject to any disclaimer, the term of this patent is extended or adjusted under 35 U.S.C. 154(b) by 85 days.

(21) Appl. No.: 17/784,378

(22) PCT Filed: Dec. 8, 2020

(86) PCT No.: PCT/EP2020/085104
§ 371 (c)(1),
(2) Date: Jun. 10, 2022

(87) PCT Pub. No.: WO2021/116114
PCT Pub. Date: Jun. 17, 2021

(65) Prior Publication Data
US 2023/0058827 A1 Feb. 23, 2023

(30) Foreign Application Priority Data
Dec. 13, 2019 (FR) ..................................... 1914368

(51) Int. Cl.
| | | |
|---|---|---|
| A61Q 5/00 | (2006.01) | |
| A61K 8/31 | (2006.01) | |
| A61K 8/33 | (2006.01) | |
| A61K 8/42 | (2006.01) | |
| A61K 8/81 | (2006.01) | |
| A61K 8/891 | (2006.01) | |
| A61K 8/898 | (2006.01) | |
| A61Q 5/06 | (2006.01) | |

(52) U.S. Cl.
CPC .............. *A61K 8/8164* (2013.01); *A61K 8/31* (2013.01); *A61K 8/33* (2013.01); *A61K 8/42* (2013.01); *A61K 8/891* (2013.01); *A61K 8/898* (2013.01); *A61Q 5/065* (2013.01); *A61K 2800/43* (2013.01); *A61K 2800/87* (2013.01); *A61K 2800/95* (2013.01)

(58) Field of Classification Search
CPC .......... A61K 8/8164; A61K 8/31; A61K 8/33; A61K 8/42; A61K 8/891; A61K 8/898; A61K 2800/43; A61K 2800/87; A61K 2800/95; A61K 8/41; A61K 8/8147; A61K 8/046; A61Q 5/065
USPC .......................................................... 8/552
See application file for complete search history.

(56) References Cited

U.S. PATENT DOCUMENTS

| | | |
|---|---|---|
| 3,579,629 A | 5/1971 | Pasero et al. |
| 3,810,977 A | 5/1974 | Evine et al. |
| 3,917,121 A | 11/1975 | Ciaffone |
| 3,966,403 A | 6/1976 | Papantoniou et al. |
| 3,966,404 A | 6/1976 | Papantoniou et al. |
| 4,185,087 A | 1/1980 | Morlino |
| 4,282,203 A | 8/1981 | Jacquet et al. |
| 4,578,266 A | 3/1986 | Tietjen et al. |
| 4,720,046 A | 1/1988 | Morane |
| 4,876,085 A * | 10/1989 | Grollier ............... A61Q 19/008 514/846 |
| 4,957,732 A | 9/1990 | Grollier et al. |
| 5,645,609 A | 7/1997 | Andrean et al. |
| 5,672,338 A | 9/1997 | Berthiaume |
| 6,106,577 A | 8/2000 | Audousset et al. |
| 8,052,762 B1 * | 11/2011 | Van Gogh ................. A61Q 5/10 8/408 |
| 2006/0128882 A1 | 6/2006 | Ichinohe |
| 2010/0120729 A1* | 5/2010 | Bayersdorfer ....... A61K 8/8158 514/169 |
| 2013/0129648 A1 | 5/2013 | Nguyen et al. |

FOREIGN PATENT DOCUMENTS

| | | |
|---|---|---|
| EP | 0186507 A2 | 7/1986 |
| EP | 0342834 A2 | 11/1989 |
| EP | 0530974 A1 | 3/1993 |
| EP | 1184426 A2 | 3/2002 |
| EP | 3311793 A1 | 4/2018 |
| FR | 1222944 A | 6/1960 |
| FR | 1564110 A | 4/1969 |
| FR | 1580545 A | 9/1969 |
| FR | 2265781 A1 | 10/1975 |
| FR | 2265782 A1 | 10/1975 |
| FR | 2439798 A1 | 5/1980 |
| FR | 2679771 A1 | 2/1993 |
| FR | 2741530 A1 | 5/1997 |
| FR | 2958540 A1 | 10/2011 |
| GB | 922457 A | 4/1963 |
| JP | 05-017710 A | 1/1993 |

(Continued)

OTHER PUBLICATIONS

Schlossman, Mitchell L., "Treated Pigments New Ways to Impart Color on the Skin," Cosmetics and Toiletries, vol. 105, Feb. 1990, pp. 53-64.
Todd, Charles, et al., "Volatile Silicone Fluids for Cosmetic Formulations," Cosmetics and Toiletries, vol. 91, Jan. 1976, pp. 29-32.
International Search Report and Written Opinion for counterpart Application No. PCT/EP2020/085104, dated Jan. 20, 2021.

*Primary Examiner* — Eisa B Elhilo
(74) *Attorney, Agent, or Firm* — THE MARBURY LAW GROUP, PLLC

(57) ABSTRACT

The subject of the present invention is an aerosol device comprising a composition for dyeing keratin fibers, comprising at least one copolymer resulting from the polymerization of at least one crotonic acid monomer or crotonic acid derivative and of at least one vinyl ester monomer, at least one fatty amine and at least one pigment. The invention also relates to a dyeing process wherein said composition is applied to keratin fibers, the operation optionally being followed by drying.

21 Claims, No Drawings

(56) References Cited

FOREIGN PATENT DOCUMENTS

| | | |
|---|---|---|
| JP | 07-258460 A | 10/1995 |
| JP | 09-188830 A | 7/1997 |
| JP | 10-158450 A | 6/1998 |
| JP | 10-158541 A | 6/1998 |
| WO | 00/76880 A1 | 12/2000 |
| WO | 2011/128255 A1 | 10/2011 |
| WO | 2018/115792 A1 | 6/2018 |
| WO | WO 2018206451 A1 * 11/2018 | ............... A61Q 5/06 |
| WO | WO 2018206453 A1 * 11/2018 | ............... A61Q 5/06 |
| WO | WO 2018206456 A1 * 11/2018 | ............... A61Q 5/06 |

* cited by examiner

AEROSOL HAIR DYEING DEVICE BASED ON A CROTONIC ACID COPOLYMER AND A FATTY AMINE

CROSS REFERENCE TO RELATED APPLICATION

This is a national stage application of PCT/EP2020/085104, filed internationally on Dec. 8, 2020, which claims priority to French Application No. 1914368, filed on Dec. 13, 2019, both of which are incorporated by reference herein in their entireties.

The subject of the present invention is an aerosol device comprising a composition for dyeing keratin fibers such as the hair, comprising at least one copolymer resulting from the polymerization of at least one crotonic acid monomer or crotonic acid derivative and of at least one vinyl ester monomer, at least one fatty amine and at least one pigment, and also a dyeing process using said composition.

TECHNICAL FIELD

In the field of dyeing keratin fibers, in particular human keratin fibers, it is already known practice to dye keratin fibers via various techniques using direct dyes or pigments for non-permanent dyeing, or dye precursors for permanent dyeing.

There are essentially three types of process for dyeing the hair:
a) "permanent" dyeing, the function of which is to afford a substantial modification to the natural color and which uses oxidation dyes which penetrate into the hair fiber and forms the dye via an oxidative condensation process;
b) non-permanent, semi-permanent or direct dyeing, which does not use the oxidative condensation process and withstands four or five shampoo washes; it consists in dyeing keratin fibers with dye compositions containing direct dyes. These dyes are colored and coloring molecules that have an affinity for keratin fibers.
c) temporary dyeing, which gives rise to a modification of the natural color of the hair that remains from one shampoo washing to the next, and which serves to enhance or correct a shade that has already been obtained. It may also be likened to a "makeup" process.

For this last type of dyeing, it is known practice to use colored polymers formed by grafting one or more dyes of azo, triphenylmethane, azine, indoamine or anthraquinone nature onto a polymer chain. These colored polymers are not entirely satisfactory, notably as regards the homogeneity of the coloring obtained and its resistance, not to mention the problems associated with their manufacture and notably with their reproducibility.

Another dyeing method consists in using pigments. Specifically, the use of pigment on the surface of keratin fibers generally makes it possible to obtain visible colorings on dark hair, since the surface pigment masks the natural color of the fiber. The use of pigment for dyeing keratin fibers is for example described in patent application FR 2 741 530.

However, compositions for temporary dyeing and/or for making-up of the hair may lead to a hair feel that is not natural and/or is uncosmetic, the hair thus dyed in particular possibly lacking softness and/or manageability and/or strand separation.

In addition, the compositions for temporary dyeing and/or for making-up of the hair can be difficult to apply, resulting in a non-uniform distribution of the dye composition on the keratin fibers and therefore a non-uniform color on the keratin fibers.

Thus, the aim of the present invention is to develop a device for dyeing keratin fibers such as the hair, allowing rapid and easy application of the dye composition to keratin fibers leading to uniform coloring over the whole of the head of hair treated, having good cosmetic properties in terms of softness or manageability of the hair and leaving the strands of hair perfectly separated. Moreover, the device according to the invention results in a coloring which does not transfer or transfers little to the skin or to textiles once dried.

DISCLOSURE OF THE INVENTION

This aim is achieved with the present invention, a subject of which is an aerosol device comprising:
at least one pressurized container comprising:
a) at least one composition comprising:
i) at least one copolymer resulting from the polymerization of at least one crotonic acid monomer or crotonic acid derivative and of at least one vinyl ester monomer,
ii) at least one fatty amine, and
iii) at least one pigment, and
b) at least one propellant, and
a means which makes it possible to deliver the composition.

Another subject of the invention is a process for dyeing keratin fibers such as the hair, comprising the application to said fibers of a composition delivered from a device as defined above, optionally followed by drying.

By using the aerosol device according to the invention, a uniform and chromatic coloring is obtained quickly and easily on the keratin fibers, such as the hair, on the whole of the head of hair. In addition, the dyed hair is softer to the touch and more manageable, and the hair strand separation is improved.

Furthermore, this composition has good transfer resistance and the deposition onto supports with which the composition comes into contact, such as the skin and/or clothing, is limited.

The term "hair with strand separation" is understood to mean hair which, after application of the composition and drying, is not stuck together (or of which all the strands are separated from each other) and thus does not form clumps of hair.

The invention is not limited to the illustrated examples. The features of the various examples may notably be combined within variants which are not illustrated.

The term "at least one" means one or more.

The aerosol device comprises at least one pressurized container comprising:
a) at least one composition comprising:
i) at least one copolymer resulting from the polymerization of at least one crotonic acid monomer or crotonic acid derivative and of at least one vinyl ester monomer,
ii) at least one fatty amine, and
iii) at least one pigment.

The composition a) according to the invention is preferably a composition for dyeing keratin fibers, such as the hair.

Crotonic Acid Copolymers:

The composition according to the invention comprises at least one copolymer resulting from the polymerization of at least one crotonic acid monomer or crotonic acid derivative and of at least one vinyl ester monomer, preferably at least two different vinyl ester monomers.

Preferably, the copolymer according to the invention is chosen from copolymers resulting from the polymerization of at least one crotonic acid monomer and of at least one vinyl ester monomer, preferably at least two different vinyl ester monomers.

The term "crotonic acid derivative" is understood to mean preferably a crotonic acid ester or a crotonic acid amide.

The term "crotonic acid derivative" is understood to mean preferably a crotonic acid ester or amide, in particular:
(i) the crotonic acid esters of formula $CH_3CH=CHCOOR'_1$ with $R'_1$ representing a linear, branched or cyclic, saturated or unsaturated, carbon-based and especially hydrocarbon-based chain, such as an alkyl, containing 1 to 30 carbon atoms, which is optionally aromatic, such as an aryl, aralkyl or alkylaryl, optionally comprising one or more functions chosen from —OH, —OR' with R' being $C_1$-$C_6$ alkyl, such as an alkoxy, —CN, —X, such as a halogen, especially Cl, F, Br or I; mention may be made, for example, of methyl crotonate and ethyl crotonate,
(ii) the crotonic acid amides of formula $CH_3CH=CHCONR'_2R''_2$ with $R'_2$ and $R''_2$, which may be identical or different, representing hydrogen or a linear, branched or cyclic, saturated or unsaturated, optionally aromatic, carbon-based and especially hydrocarbon-based chain, such as an alkyl, containing 1 to 30 carbon atoms, optionally comprising one or more functions chosen from —OH, —OR' with R' being $C_1$-$C_6$ alkyl, such as an alkoxy, —CN, —X, such as a halogen, especially Cl, F, Br or I.

The vinyl ester monomer(s) may be chosen from the compounds of formula $CH_2=C(H)—O—CO—R'_3$ with $R'_3$ representing a linear, branched or cyclic, saturated or unsaturated, optionally aromatic, carbon-based and especially hydrocarbon-based chain, containing 1 to 30 carbon atoms, optionally comprising one or more functions chosen from —OH, —OR' with R' being $C_1$-$C_6$ alkyl (alkoxy), —CN, -X (halogen, especially Cl, F, Br or I).

Mention may be made especially of vinyl acetate, vinyl propionate, vinyl butyrate (or butanoate), vinyl ethylhexanoate, vinyl neononanoate and vinyl neododecanoate, vinyl neodecanoate, vinyl pivalate, vinyl cyclohexanoate, vinyl benzoate, vinyl 4-tert-butylbenzoate and vinyl trifluoroacetate.

Preferably, the copolymer according to the invention is chosen from copolymers resulting from the polymerization of at least one crotonic acid monomer and of at least two different vinyl ester monomers, said vinyl ester monomers preferably being chosen from vinyl acetate, vinyl propionate, vinyl butyrate (or butanoate), vinyl ethylhexanoate, vinyl neononanoate and vinyl neododecanoate, vinyl neodecanoate, vinyl pivalate, vinyl cyclohexanoate, vinyl benzoate, vinyl 4-tert-butylbenzoate and vinyl trifluoroacetate, preferably from vinyl acetate, vinyl propionate and vinyl neodecanoate, better still from vinyl acetate and vinyl neodecanoate.

More particularly, the copolymer according to the invention is chosen from copolymers resulting from the polymerization of crotonic acid, vinyl acetate and vinyl propionate, copolymers resulting from the polymerization of crotonic acid, vinyl acetate and vinyl neodecanoate, and mixtures thereof.

According to a particular embodiment, the copolymer of the composition according to the invention is a crotonic acid/vinyl acetate/vinyl neodecanoate terpolymer.

The copolymers according to the invention may optionally comprise other monomers such as allylic or methallylic esters, or vinyl ethers. These polymers may optionally be grafted or crosslinked.

Such polymers are described, inter alia, in French patents FR1 222 944, FR1 580 545, FR2 265 782, FR2 265 781, FR1 564 110 and FR2 439 798. Commercial products which fall into this category are the products Resyn® 28-2930 and 28-1310 sold by the company AkzoNobel (INCI names: VA/crotonates/vinyl decanoate copolymer and VA/crotonates copolymer, respectively). Mention may also be made of the products Luviset® CA 66 sold by the company BASF, Aristoflex® A60 sold by the company Clariant (INCI name: VA/crotonates copolymer) and Mexomere® PW or PAM sold by the company Chimex (INCI name: VA/vinyl butyl benzoate/crotonates copolymer).

The total amount of crotonic acid copolymer(s) resulting from the polymerization of at least one crotonic acid monomer or crotonic acid derivative and of at least one vinyl ester monomer according to the invention can range from 0.05% to 15% by weight relative to the weight of the composition, preferably from 0.1% to 10% by weight relative to the weight of the composition, preferably from 0.1% to 7% by weight relative to the weight of the composition.

Fatty Amine:

The composition according to the invention comprises at least one fatty amine.

The term "fatty amines" is understood to mean primary, secondary or tertiary fatty amines, which are optionally (poly)oxyalkylenated, or salts thereof. The fatty amines generally comprise at least one $C_6$-$C_{30}$ hydrocarbon-based chain. Preferably, the fatty amines according to the invention are not quaternized. Preferably, the fatty amines according to the invention are not (poly)oxyalkylenated.

Preferably, the composition according to the invention comprises at least one fatty amine comprising at least one $C_6$-$C_{30}$ hydrocarbon-based chain.

Preferably, the composition according to the invention comprises at least one fatty amine chosen from tertiary fatty amines.

More preferentially, the composition according to the invention comprises one or more tertiary fatty amines chosen from fatty amidoamines.

The fatty amines that may be used in the context of the invention may be chosen from the fatty amines having the formula (K) below:

[Chem. 1]

 (K)

wherein:
R represents a monovalent hydrocarbon-based radical containing from 6 to 30 carbon atoms, preferably from 8 to 24 carbon atoms, and in particular a linear or branched, saturated or unsaturated and substituted or unsubstituted $C_6$-$C_{30}$, preferably $C_8$-$C_{24}$, alkyl radical, preferably a linear or branched $C_6$-$C_{30}$, better still $C_8$-$C_{24}$, alkyl radical, or a linear or branched $C_6$-$C_{30}$, preferably $C_8$-$C_{24}$, alkenyl radical; and
R', which may be identical or different, represent a linear or branched, saturated or unsaturated and substituted or unsubstituted monovalent hydrocarbon-based radical containing less than 6 carbon atoms, preferably from 1 to 4 carbon atoms, preferably a methyl radical.

The fatty amines corresponding to formula (K) are chosen, for example, from dimethyllauramine, dimethylbehenamine, dimethylcocamine, dimethylmyristamine, dimethylpalmitamine, dimethylstearamine, dimethyltallowamine, dimethylsoyamine, and mixtures thereof.

The fatty amines that may be used in the context of the invention may also be chosen from fatty amidoamines, preferably the fatty amidoamines having the formula (L) below:

[Chem. 2]

R—CO—N(H)—R"—N(R')$_2$ (L)

wherein:
R represents a monovalent hydrocarbon-based radical containing from 5 to 29 carbon atoms, preferably from 7 to 23 carbon atoms, and in particular a linear or branched, saturated or unsaturated and substituted or unsubstituted $C_5$-$C_{29}$, preferably $C_7$-$C_{23}$, alkyl radical, preferably a linear or branched $C_5$-$C_{29}$, better still $C_5$-$C_{23}$, alkyl radical, or a linear or branched $C_5$-$C_{29}$, preferably $C_7$-$C_{23}$, alkenyl radical;
R", which may be identical or different, represent a divalent hydrocarbon-based radical containing less than 6 carbon atoms, preferably 2 or 3 carbon atoms; and
R', which may be identical or different, represent a linear or branched, saturated or unsaturated and substituted or unsubstituted monovalent hydrocarbon-based radical containing less than 6 carbon atoms, preferably from 1 to 4 carbon atoms, preferably a methyl radical.

The fatty amines corresponding to formula (L) are chosen, for example, from oleamidopropyl dimethylamine, stearamidopropyl dimethylamine sold by the company Inolex Chemical Company under the name Lexamine S13, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamidopropyl dimethylamine, soyamidopropyl dimethylamine, avocadoamidopropyl dimethylamine, cocamidopropyl dimethylamine, minkamidopropyl dimethylamine, oatamidopropyl dimethylamine, sesamidopropyl dimethylamine, tallamidopropyl dimethylamine, olivamidopropyl dimethylamine, palmitamidopropyl dimethylamine, stearamidoethyldiethylamine, brassicamidopropyl dimethylamine, and mixtures thereof.

Preferably, the fatty amine is stearamidopropyl dimethylamine.

Preferably, the fatty amine(s) according to the invention are chosen from fatty amidoamines, preferentially from the fatty amidoamines of formula (L).

Preferably, the composition according to the invention comprises a stearamidopropyl dimethylamine.

Preferably, the fatty amine(s) is (are) present in a total amount ranging from 0.001% to 10% by weight, preferably from 0.005% to 5% by weight, better still from 0.01% to 3% by weight relative to the total weight of the composition.

Preferably, the weight ratio of the total amount of copolymer(s) of crotonic acid or crotonic acid derivative according to the invention to the total amount of fatty amine(s) ranges from 0.1 to 10, more preferentially from 0.5 to 8, better still from 1 to 5.

Silicone

The composition may comprise at least one silicone. Preferably, the composition comprises at least two different silicones.

Preferably, the composition comprises at least one non-amino silicone and at least one amino silicone.

The silicones may be solid or liquid at 25° C. and atmospheric pressure (1.013×10$^5$ Pa), and volatile or nonvolatile.

The silicones that may be used may be soluble or insoluble in the composition according to the invention; they may be in the form of oil, wax, resin or gum; silicone oils are preferred.

Silicones are notably described in detail in Walter Noll's *Chemistry and Technology of Silicones* (1968), Academic Press.

Preferably, the composition contains one or more silicones that are liquid at 25° C. and atmospheric pressure (1.013×10$^5$ Pa).

The volatile silicones may be chosen from those with a boiling point of between 60° C. and 260° C. (at atmospheric pressure), more particularly from: i) cyclic polydialkylsiloxanes including from 3 to 7, preferably 4 to 5, silicon atoms, such as
octamethylcyclotetrasiloxane and decamethylcyclopentasiloxane.

Mention may be made of the products sold under the name Volatile Silicone 7207 by Union Carbide or Silbione 70045 V 2 by Rhodia, Volatile Silicone 7158 by Union Carbide or Silbione 70045 V 5 by Rhodia.
cyclocopolymers of the dimethylsiloxane/methylalkylsiloxane type having the chemical structure:

[Chem. 3]

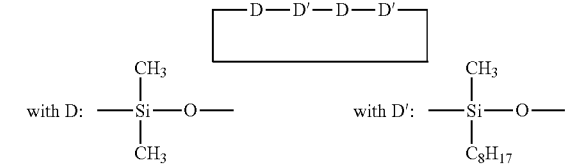

Preferably cyclomethylsiloxane.
Mention may be made of Volatile Silicone FZ 3109 sold by the company Union Carbide.
mixtures of cyclic silicones with silicon-derived organic compounds, such as the mixture of octamethylcyclotetrasiloxane and of tetratrimethylsilylpentaerythritol (50/50) and the mixture of octamethylcyclotetrasiloxane and of 1,1'-oxy(2,2,2',2',3,3'-hexatrimethylsilyloxy)bisneopentane;
ii) linear polydialkylsiloxanes containing 2 to 9 silicon atoms, which generally have a viscosity of less than or equal to 5×10$^{-6}$ m$^2$/s at 25° C., such as decamethyltetrasiloxane.

Other silicones belonging to this category are described in the article published in Cosmetics and Toiletries, Vol. 91, January 76, pages 27-32, Todd & Byers "Volatile Silicone Fluids for Cosmetics"; mention may be made of the product sold under the name SH 200 by the company Toray Silicone.

Among the nonvolatile silicones, mention may be made, alone or as a mixture, of polydialkylsiloxanes and notably polydimethylsiloxanes (PDMS), polydiarylsiloxanes, polyalkylarylsiloxanes, silicone gums and resins, and also organopolysiloxanes (or organomodified polysiloxanes, or alternatively organomodified silicones) which are polysiloxanes including in their structure one or more organofunctional groups, generally attached via a hydrocarbon-based group, and preferably chosen from aryl groups, amine groups, alkoxy groups and polyoxyethylene or polyoxypropylene groups. Preferably, the nonvolatile silicones are chosen from poly dimethyl/methylsiloxanes which are optionally oxyethylenated and oxypropylenated.

The organomodified silicones may be polydiarylsiloxanes, notably polydiphenylsiloxanes, and polyalkylarylsiloxanes, functionalized with the organofunctional groups mentioned previously. The polyalkylarylsiloxanes are particularly chosen from linear and/or branched polydimethyl/methylphenylsiloxanes and polydimethyl/diphenylsiloxanes.

Among the organomodified silicones, mention may be made of organopolysiloxanes including:

polyoxyethylene and/or polyoxypropylene groups optionally including C6-C24 alkyl groups, such as dimethicone copolyols, and notably those sold by the company Dow Corning under the name DC 1248 or the oils Silwet® L 722, L 7500, L 77 and L 711 from the company Union Carbide; or alternatively (C12)alkylmethicone copolyols, and notably those sold by the company Dow Corning under the name Q2-5200;

substituted or unsubstituted amine groups, in particular C1-C4 aminoalkyl groups; mention may be made of the products sold under the name GP4 Silicone Fluid and GP7100 by the company Genesee, or under the names Q2-8220 and DC929 or DC939 by the company Dow Corning;

thiol groups, such as the products sold under the names GP 72 A and GP 71 from Genesee;

alkoxylated groups, such as the product sold under the name Silicone Copolymer F-755 by SWS Silicones and Abil Wax® 2428, 2434 and 2440 by the company Goldschmidt;

hydroxylated groups, for instance polyorganosiloxanes bearing a hydroxyalkyl function;

acyloxyalkyl groups, such as the polyorganosiloxanes described in U.S. Pat. No. 4,957,732;

anionic groups of the carboxylic acid type, as described, for example, in EP186507, or of the alkylcarboxylic type, such as the product X-22-3701E from the company Shin-Etsu; or alternatively of the 2-hydroxyalkylsulfonate or 2-hydroxyalkylthiosulfate type, such as the products sold by the company Goldschmidt under the names Abil® S201 and Abil® S255;

hydroxyacylamino groups, such as the polyorganosiloxanes described in patent application EP342834; mention may be made, for example, of the product Q2-8413 from the company Dow Corning.

The silicones may also be chosen from polydialkylsiloxanes, among which mention may be made mainly of polydimethylsiloxanes bearing trimethylsilyl end groups. Among these polydialkylsiloxanes, mention may be made of the following commercial products:

the Silbione® oils of the 47 and 70 047 series or the Mirasil® oils sold by Rhodia, for instance the oil 70 047 V 500 000;

the oils of the Mirasil® series sold by the company Rhodia;

the oils of the 200 series from the company Dow Corning, such as DC200 with a viscosity of 60 000 mm²/s;

the Viscasil® oils from General Electric and certain oils of the SF series (SF 96, SF 18) from General Electric.

Mention may also be made of polydimethylsiloxanes bearing dimethylsilanol end groups, known under the name dimethiconol (CTFA), such as the oils of the 48 series from the company Rhodia.

In this category of polydialkylsiloxanes, mention may also be made of the products sold under the names Abil Wax® 9800 and 9801 by the company Goldschmidt, which are poly(C1-C20)dialkylsiloxanes.

Products that may be used more particularly in accordance with the invention are mixtures such as:

mixtures formed from a polydimethylsiloxane with a hydroxy-terminated chain, or dimethiconol (CTFA), and from a cyclic polydimethylsiloxane, also known as cyclomethicone (CTFA), such as the product Q2-1401 sold by the company Dow Corning, mixtures formed from a polydimethylsiloxane with a hydroxy-terminated chain, or dimethiconol (CTFA), and from a cyclic polydimethylsiloxane, also known as dimethicone (CTFA), such as the product Xiameter® PMX-1503 Fluid sold by the company Dow Corning.

The polyalkylarylsiloxanes are chosen particularly from linear and/or branched polydimethyl/methylphenylsiloxanes and polydimethyl/diphenylsiloxanes with a viscosity of from $1\times10^{-5}$ to $5\times10^{-2}$ m²/s at 25° C.

Among these polyalkylarylsiloxanes, mention may be made of the products sold under the following names:

the Silbione® oils of the 70 641 series from Rhodia;

the oils of the Rhodorsil® 70 633 and 763 series from Rhodia;

the Dow Corning 556 Cosmetic Grade Fluid oil from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Preferably, the composition according to the invention comprises at least one non-amino silicone, more preferentially at least one non-amino silicone with the INCI name dimethicone.

The composition according to the invention preferably comprises one or more amino silicones. The term "amino silicone" denotes any silicone including at least one primary, secondary or tertiary amine or a quaternary ammonium group.

Preferably, the composition comprises at least one amino silicone.

The weight-average molecular weights of these amino silicones may be measured by gel permeation chromatography (GPC) at ambient temperature (25° C.), as polystyrene equivalent. The columns used are p styragel columns. The eluent is THF and the flow rate is 1 ml/minute. 200 μl of a 0.5% by weight solution of silicone in THF are injected. Detection is performed by refractometry and UV-metry.

Preferably, the amino silicone(s) that may be used in the context of the invention are chosen from:

a) the polysiloxanes corresponding to formula (A):

[Chem. 4]

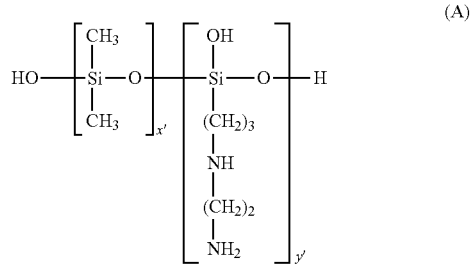

(A)

wherein x' and y' are integers such that the weight-average molecular weight (Mw) is between 5000 and 500 000 approximately;

b) the amino silicones corresponding to formula (B):

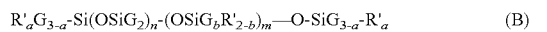  (B)

wherein:

G, which may be identical or different, denotes a hydrogen atom or a phenyl, OH or $C_1$-$C_5$ alkyl group, for example methyl, or a $C_1$-$C_5$ alkoxy, for example methoxy, a, which may be identical or different, denotes 0 or an integer from 1 to 3, in particular 0, b denotes 0 or 1, in particular 1, m and n are numbers such that the sum (n+m) varies from 1 to 2000, in particular from 50 to 150, n possibly denoting a number from 0 to 1999 and notably from 49 to 149, and m possibly denoting a number from 1 to 2000 and notably from 1 to 10;

R', which may be identical or different, denotes a monovalent radical of formula —$C_qH_{2q}$L wherein q is a number ranging from 2 to 8 and L is an optionally quaternized amino group chosen from the following groups:
—N(R")$_2$; —N+(R")$_3$ A—; —NR"-Q-N(R")$_2$ and —NR"-Q-N+(R")$_3$ A—, wherein R", which may be identical or different, denotes hydrogen, phenyl, benzyl, or a saturated monovalent hydrocarbon-based radical, for example a $C_1$-$C_{20}$ alkyl radical; Q denotes a linear or branched group of formula $C_rH_{2r}$, r being an integer ranging from 2 to 6, preferably from 2 to 4; and A— represents a cosmetically acceptable anion, especially a halide anion such as a fluoride, chloride, bromide or iodide anion.

Preferably, the amino silicones are chosen from the amino silicones of formula (B). Preferably, the amino silicones of formula (B) are chosen from the amino silicones corresponding to formulae (C), (D), (E), (F) and/or (G) below. Preferably, the amino silicones of formula (B) are chosen from the amino silicones corresponding to formula (F).

According to a first embodiment, the amino silicones corresponding to formula (B) are chosen from the silicones known as "trimethylsilyl amodimethicone" corresponding to formula (C):

[Chem. 5]

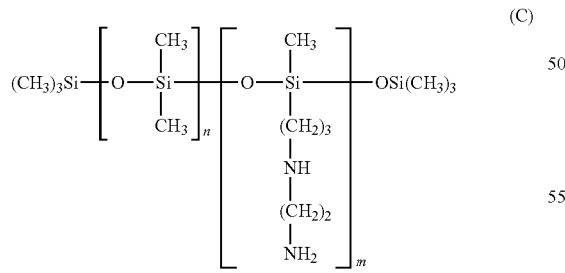  (C)

wherein m and n are numbers such that the sum (n+m) varies from 1 to 2000, in particular from 50 to 150, n possibly denoting a number from 0 to 1999 and notably from 49 to 149, and m possibly denoting a number from 1 to 2000 and notably from 1 to 10.

According to a second embodiment, the amino silicones corresponding to formula (B) are chosen from the silicones of formula (D) below:

[Chem. 6]

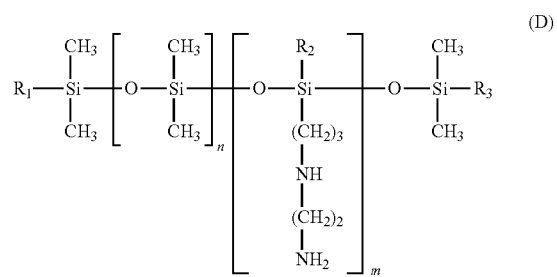  (D)

wherein:

m and n are numbers such that the sum (n+m) varies from 1 to 1000, in particular from 50 to 250 and more particularly from 100 to 200, n possibly denoting a number from 0 to 999 and notably from 49 to 249 and more particularly from 125 to 175 and m possibly denoting a number from 1 to 1000, notably from 1 to 10, more particularly from 1 to 5;

$R_1$, $R_2$ and $R_3$, which may be identical or different, represent a hydroxyl or $C_1$-$C_4$ alkoxy radical, at least one of the radicals $R_1$ to $R_3$ denoting an alkoxy radical.

Preferably, the alkoxy radical is a methoxy radical.

The hydroxy/alkoxy mole ratio preferably ranges from 0.2:1 to 0.4:1 and preferably from 0.25:1 to 0.35:1 and more particularly is equal to 0.3:1.

The weight-average molecular weight (Mw) of these silicones preferably ranges from 2000 to 1 000 000, more particularly from 3500 to 200 000.

According to a third embodiment, the amino silicones corresponding to formula (B) are chosen from the silicones of formula (E) below:

[Chem. 7]

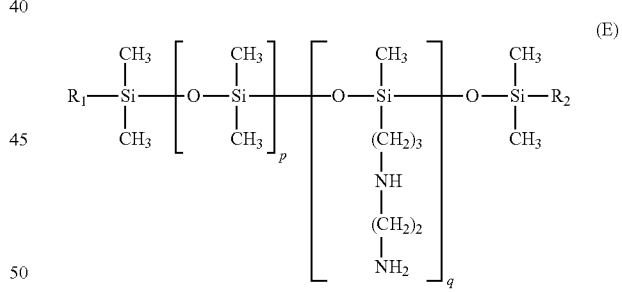  (E)

wherein:

p and q are numbers such that the sum (p+q) varies from 1 to 1000, in particular from 50 to 350 and more particularly from 150 to 250; p possibly denoting a number from 0 to 999 and notably from 49 to 349 and more particularly from 159 to 239, and q possibly denoting a number from 1 to 1000, notably from 1 to 10 and more particularly from 1 to 5;

$R_1$ and $R_2$, which are different, represent a hydroxyl or $C_1$-$C_4$ alkoxy radical, at least one of the radicals $R_1$ or $R_2$ denoting an alkoxy radical.

Preferably, the alkoxy radical is a methoxy radical.

The hydroxy/alkoxy mole ratio generally ranges from 1:0.8 to 1:1.1 and preferably from 1:0.9 to 1:1 and more particularly is equal to 1:0.95.

The weight-average molecular weight (Mw) of the silicone preferably ranges from 2000 to 200 000 and even more particularly from 5000 to 100 000 and more particularly from 10 000 to 50 000.

The commercial products comprising silicones of structure (D) or (E) may include in their composition one or more other amino silicones of which the structure is different from formula (D) or (E).

A product containing amino silicones of structure (D) is made available by the company Wacker under the name Belsil® ADM 652.

A product containing amino silicones of structure (E) is made available by Wacker under the name Fluid WR 1300@.

When these amino silicones are used, one particularly advantageous embodiment consists in using them in the form of an oil-in-water emulsion. The oil-in-water emulsion may comprise one or more surfactants. The surfactants may be of any nature but are preferably cationic and/or nonionic. The number-mean size of the silicone particles in the emulsion generally ranges from 3 nm to 500 nanometers. Preferably, notably as amino silicones of formula (E), use is made of microemulsions with a mean particle size ranging from 5 nm to 60 nanometers (limits included) and more particularly from 10 nm to 50 nanometers (limits included). Thus, use may be made according to the invention of the amino silicone microemulsions of formula (E) made available under the names Finish CT 96 E® or SLM 28020@ by the company Wacker.

According to a fourth embodiment, the amino silicones corresponding to formula (B) are chosen from the silicones of formula (F) below:

[Chem. 8]

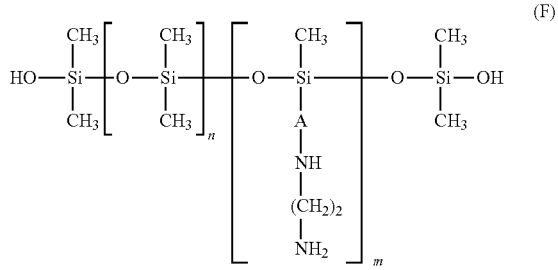

(F)

wherein:

m and n are numbers such that the sum (n+m) ranges from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably linear.

The weight-average molecular weight (Mw) of these amino silicones preferably ranges from 2000 to 1 000 000 and even more particularly from 3500 to 200 000.

A silicone corresponding to this formula is, for example, the Xiameter MEM 8299 Emulsion from Dow Corning (INCI name: amodimethicone and trideceth-6 and cetrimonium chloride).

According to a fifth embodiment, the amino silicones corresponding to formula (B) are chosen from the silicones of formula (G) below:

[Chem. 9]

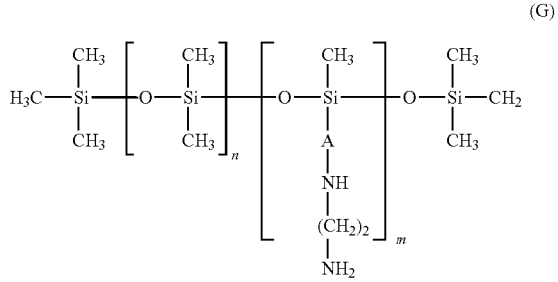

(G)

wherein:

m and n are numbers such that the sum (n+m) varies from 1 to 2000 and in particular from 50 to 150, n possibly denoting a number from 0 to 1999 and notably from 49 to 149, and m possibly denoting a number from 1 to 2000 and notably from 1 to 10;

A denotes a linear or branched alkylene radical containing from 4 to 8 carbon atoms and preferably 4 carbon atoms. This radical is preferably branched.

The weight-average molecular weight (Mw) of these amino silicones preferably ranges from 500 to 1 000 000 and even more particularly from 1000 to 200 000.

A silicone corresponding to this formula is, for example, DC2-8566 Amino Fluid from Dow Corning.

c) the amino silicones corresponding to formula (H):

[Chem. 10]

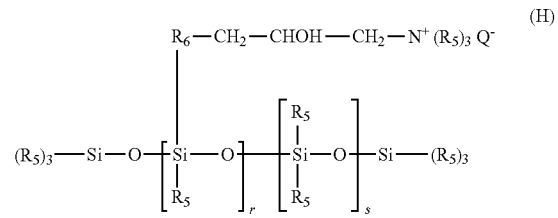

(H)

wherein:

$R_5$ represents a monovalent hydrocarbon-based radical containing from 1 to 18 carbon atoms, and in particular a $C_1$-$C_{15}$ alkyl or $C_2$-$C_{15}$ alkenyl, for example methyl, radical;

$R_6$ represents a divalent hydrocarbon-based radical, in particular a $C_1$-$C_{18}$ alkylene radical or a divalent $C_1$-$C_{15}$, for example $C_1$-$C_5$, alkyleneoxy radical linked to the Si via an SiC bond;

$Q^-$ is an anion, such as a halide ion, in particular a chloride ion, or an organic acid salt, in particular an acetate;

r represents a mean statistical value ranging from 2 to 20, in particular from 2 to 8;

s represents a mean statistical value ranging from 20 to 200, in particular from 20 to 50.

Such amino silicones are notably described in patent U.S. Pat. No. 4,185,087.

d) the quaternary ammonium silicones of formula (I):

[Chem. 11]

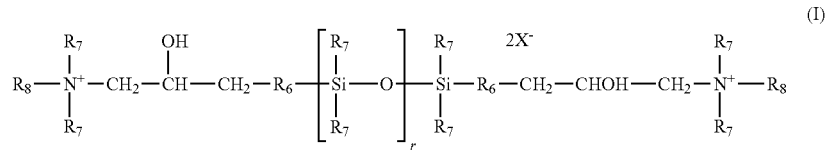

wherein:
R$_7$, which may be identical or different, represent a monovalent hydrocarbon-based radical containing from 1 to 18 carbon atoms, and in particular a $C_1$-$C_{15}$ alkyl radical, a $C_2$-$C_{18}$ alkenyl radical or a ring containing 5 or 6 carbon atoms, for example methyl;
R$_6$ represents a divalent hydrocarbon-based radical, notably a $C_1$-$C_{18}$ alkylene radical or a divalent $C_1$-$C_{15}$, for example $C_1$-$C_5$, alkyleneoxy radical linked to the Si via an SiC bond;
R8, which may be identical or different, represent a hydrogen atom, a monovalent hydrocarbon-based radical containing from 1 to 18 carbon atoms, and in particular a $C_1$-$C_{15}$ alkyl radical, a $C_2$-$C_{18}$ alkenyl radical or a —R$_6$—N(H)COR$_7$ radical;
X$^-$ is an anion, such as a halide ion, in particular a chloride ion, or an organic acid salt, in particular an acetate;
r represents a mean statistical value ranging from 2 to 200, in particular from 5 to 100.

These silicones are described, for example, in patent application EP-A-0530974.

e) the amino silicones of formula (J):

[Chem. 12]

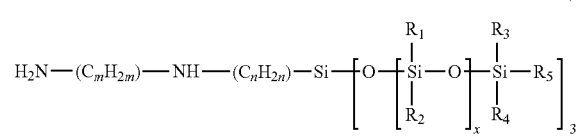

wherein:
R$_1$, R$_2$, R$_3$ and R$_4$, which may be identical or different, denote a $C_1$-$C_4$ alkyl radical or a phenyl group,
R$_5$ denotes a $C_1$-$C_4$ alkyl radical or a hydroxyl group,
n is an integer ranging from 1 to 5,
m is an integer ranging from 1 to 5, and
x is chosen such that the amine number ranges from 0.01 to 1 meq/g.

f) the multiblock polyoxyalkylenated amino silicones of type (AB)n, A being a polysiloxane block and B being a polyoxyalkylenated block including at least one amine group.

Said silicones are preferably formed from repeating units having the following general formulae:

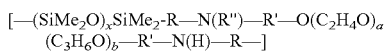

or alternatively

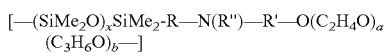

wherein:
a is an integer greater than or equal to 1, preferably ranging from 5 to 200, more particularly ranging from 10 to 100;
b is an integer of between 0 and 200, preferably ranging from 4 to 100, more particularly between 5 and 30;
x is an integer ranging from 1 to 10 000, more particularly from 10 to 5000;
R" is a hydrogen atom or a methyl;
R, which may be identical or different, represent a linear or branched divalent $C_2$-$C_{12}$ hydrocarbon-based radical, optionally including one or more heteroatoms such as oxygen; preferably, R denotes an ethylene radical, a linear or branched propylene radical, a linear or branched butylene radical or a radical $CH_2CH_2CH_2OCH_2CH(OH)CH_2$—; preferentially, R denotes a radical $CH_2CH_2CH_2OCH_2CH(OH)CH_2$—;
R', which may be identical or different, represent a linear or branched divalent $C_2$-$C_{12}$ hydrocarbon-based radical, optionally including one or more heteroatoms such as oxygen; preferably, R' denotes an ethylene radical, a linear or branched propylene radical, a linear or branched butylene radical or a radical $CH_2CH_2CH_2OCH_2CH(OH)CH_2$—; preferentially, R' denotes —$CH(CH_3)$—$CH_2$—.

The siloxane blocks preferably represent 50 mol % to 95 mol % of the total weight of the silicone, more particularly from 70 mol % to 85 mol %.

The amine content is preferably between 0.02 and 0.5 meq/g of copolymer in a 30% solution in dipropylene glycol, more particularly between 0.05 and 0.2.

The weight-average molecular weight (Mw) of the silicone is preferably between 5000 and 1 000 000, more particularly between 10 000 and 200 000.

Mention may in particular be made of the silicones sold under the names Silsoft A– 843 or Silsoft A+ by Momentive.

g) and mixtures thereof.

Preferably, the composition according to the invention comprises at least one amino silicone having the INCI name amodimethicone, preferably as an oil-in-water emulsion with surfactants.

Preferably, the composition according to the invention comprises at least one amino silicone having the INCI name amodimethicone as an oil-in-water emulsion with surfactants, with the INCI name trideceth-10.

Preferably, the composition comprises at least one non-amino silicone and/or at least one amino silicone.

Preferably, the composition comprises at least one non-amino silicone chosen from the non-amino silicones with the INCI name dimethicone, and/or at least one amino silicone with the INCI name amodimethicone.

Even more preferentially, the composition comprises at least one non-amino silicone with the INCI name dimethicone, and at least one amino silicone with the INCI name amodimethicone.

The silicone(s) may be present in a total amount of at least 0.01% by weight relative to the total weight of the composition, preferably at least 0.05% by weight, more preferentially at least 0.1% by weight relative to the total weight of the composition.

The silicone(s) may be present in a total amount which may range from 0.01% to 10% by weight relative to the total weight of the composition, preferably from 0.05% to 8% by weight, more preferentially from 0.1% to 5%, by weight relative to the total weight of the composition.

When the composition according to the invention comprises one or more amino silicones, the total amount of amino silicone(s) may range from 0.001% to 5% by weight, preferably from 0.005% to 4% by weight, better still from 0.01% to 3% by weight relative to the total weight of the composition.

When the composition according to the invention comprises one or more non-amino silicones, the total amount of non-amino silicone(s) may range from 0.001% to 5% by weight, preferably from 0.005% to 4% by weight, better still from 0.01% to 3% by weight relative to the total weight of the composition.

Preferably, the weight ratio of the total amount of copolymer(s) of crotonic acid or crotonic acid derivative according to the invention to the total amount of silicone(s) ranges from 0.1 to 10, more preferentially from 0.5 to 8, better still from 1 to 5.

When the composition according to the invention comprises one or more amino silicones, the weight ratio of the total amount of copolymer(s) of crotonic acid or crotonic acid derivative according to the invention to the total amount of amino silicone(s) ranges from 0.1 to 10, more preferentially from 0.5 to 8, better still from 1 to 5.

Pigment:

The composition according to the invention comprises at least one pigment.

The term "pigment" is understood to mean any pigment that gives color to keratin materials. Their solubility in water at 25° C. and at atmospheric pressure (760 mmHg) is less than 0.05% by weight and preferably less than 0.01%.

The pigments that may be used are notably chosen from the organic and/or mineral pigments known in the art, notably those that are described in Kirk-Othmer's Encyclopedia of Chemical Technology and in Ullmann's Encyclopedia of Industrial Chemistry.

They may be natural, of natural origin, or non-natural.

These pigments may be in pigment powder or paste form. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" is understood to mean any pigment that satisfies the definition in Ullmann's encyclopedia in the chapter on inorganic pigments. Among the mineral pigments that are useful in the present invention, mention may be made of iron oxides or chromium oxides, manganese violet, ultramarine blue, chromium hydrate, ferric blue and titanium oxide.

The pigment may be an organic pigment. The term "organic pigment" is understood to mean any pigment that satisfies the definition in Ullmann's encyclopedia in the chapter on organic pigments.

The organic pigment may notably be chosen from nitroso, nitro, azo, xanthene, pyrene, quinoline, anthraquinone, triphenylmethane, fluorane, phthalocyanine, metal-complex, isoindolinone, isoindoline, quinacridone, perinone, perylene, diketopyrrolopyrrole, indigo, thioindigo, dioxazine, triphenylmethane and quinophthalone compounds.

In particular, the white or colored organic pigments may be chosen from carmine, carbon black, aniline black, azo yellow, quinacridone, phthalocyanine blue, the blue pigments codified in the Color Index under the references CI 42090, 69800, 69825, 74100, 74160, the yellow pigments codified in the Color Index under the references CI 11680, 11710, 19140, 20040, 21100, 21108, 47000, 47005, the green pigments codified in the Color Index under the references CI 61565, 61570, 74260, the orange pigments codified in the Color Index under the references CI 11725, 45370, 71105, the red pigments codified in the Color Index under the references CI 12085, 12120, 12370, 12420, 12490, 14700, 15525, 15580, 15620, 15630, 15800, 15850, 15865, 15880, 26100, 45380, 45410, 58000, 73360, 73915, 75470, the pigments obtained by oxidative polymerization of indole or phenol derivatives as described in patent FR 2 679 771.

Examples that may also be mentioned include pigment pastes of organic pigments, such as the products sold by the company Hoechst under the names:

Cosmenyl Yellow IOG: Yellow 3 pigment (CI 11710);
Cosmenyl Yellow G: Yellow 1 pigment (CI 11680);
Cosmenyl Orange GR: Orange 43 pigment (CI 71105);
Cosmenyl Red R: Red 4 pigment (CI 12085);
Cosmenyl Carmine FB: Red 5 pigment (CI 12490);
Cosmenyl Violet RL: Violet 23 pigment (CI 51319);
Cosmenyl Blue A2R: Blue 15.1 pigment (CI 74160);
Cosmenyl Green GG: Green 7 pigment (CI 74260);
Cosmenyl Black R: Black 7 pigment (CI 77266).

The pigments in accordance with the invention may also be in the form of composite pigments, as described in patent EP 1 184 426. These composite pigments may be composed notably of particles including a mineral core, at least one binder for attaching the organic pigments to the core, and at least one organic pigment which at least partially covers the core.

The organic pigment may also be a lake. The term "lake" is understood to mean dyes adsorbed onto insoluble particles, the assembly thus obtained remaining insoluble during use.

The inorganic substrates onto which the dyes are adsorbed are, for example, alumina, silica, calcium sodium borosilicate or calcium aluminum borosilicate and aluminum.

Among the dyes, mention may be made of carminic acid. Mention may also be made of the dyes known under the following names: D & C Red 21 (CI 45 380), D & C Orange 5 (CI 45 370), D & C Red 27 (CI 45 410), D & C Orange 10 (CI 45 425), D & C Red 3 (CI 45 430), D & C Red 4 (CI 15 510), D & C Red 33 (CI 17 200), D & C Yellow 5 (CI 19 140), D & C Yellow 6 (CI 15 985), D & C Green (CI 61 570), D & C Yellow 1 0 (CI 77 002), D & C Green 3 (CI 42 053), D & C Blue 1 (CI 42 090).

An example of a lake that may be mentioned is the product known under the following name: D & C Red 7 (CI 15 850:1).

The pigment may also be a pigment with special effects. The term "pigments with special effects" is understood to mean pigments that generally create a colored appearance (characterized by a certain shade, a certain vivacity and a certain level of luminance) that is non-uniform and that changes as a function of the conditions of observation (light, temperature, angles of observation, etc.). They thereby differ from colored pigments, which afford a standard uniform opaque, semi-transparent or transparent shade.

Several types of pigments with special effects exist: those with a low refractive index, such as fluorescent or photochromic pigments, and those with a higher refractive index, such as nacres, interference pigments or glitter flakes.

Examples of pigments with special effects that may be mentioned include nacreous pigments such as mica coated with titanium or with bismuth oxychloride, colored nacreous pigments such as mica coated with titanium and with iron oxides, mica coated with iron oxide, mica coated with titanium and notably with ferric blue or with chromium oxide, mica coated with titanium and with an organic pigment of the abovementioned type, and also nacreous pigments based on bismuth oxychloride. Nacreous pigments that may be mentioned include the Cellini nacres sold by BASF (mica-TiO2-lake), Prestige sold by Eckart (mica-TiO2), Prestige Bronze sold by Eckart (mica-Fe2O3), and Colorona sold by Merck (mica-TiO2-Fe2O3).

Mention may also be made of the gold-colored nacres sold notably by the company BASF under the name Brilliant gold 212G (Timica), Gold 222C (Cloisonne), Sparkle gold (Timica), Gold 4504 (Chromalite) and Monarch gold 233X (Cloisonne); the bronze nacres sold notably by the company Merck under the name Bronze fine (17384) (Colorona) and Bronze (17353) (Colorona) and by the company BASF under the name Super bronze (Cloisonne); the orange nacres sold notably by the company BASF under the name Orange 363C (Cloisonne) and Orange MCR 101 (Cosmica) and by the company Merck under the name Passion orange (Colorona) and Matte orange (17449) (Microna); the brown nacres sold notably by the company BASF under the name Nu-antique copper 340XB (Cloisonne) and Brown CL4509 (Chromalite); the nacres with a copper tint sold notably by the company BASF under the name Copper 340A (Timica); the nacres with a red tint sold notably by the company Merck under the name Sienna fine (17386) (Colorona); the nacres with a yellow tint sold notably by the company BASF under the name Yellow (4502) (Chromalite); the red nacres with a gold tint sold notably by the company BASF under the name Sunstone G012 (Gemtone); the pink nacres sold notably by the company BASF under the name Tan opale G005 (Gemtone); the black nacres with a gold tint sold notably by the company BASF under the name Nu antique bronze 240 AB (Timica), the blue nacres sold notably by the company Merck under the name Matte blue (17433) (Microna), the white nacres with a silvery tint sold notably by the company Merck under the name Xirona Silver, and the golden-green pink-orange nacres sold notably by the company Merck under the name Indian summer (Xirona), and mixtures thereof.

Still as examples of nacres, mention may also be made of particles including a borosilicate substrate coated with titanium oxide.

Particles comprising a glass substrate coated with titanium oxide are notably sold under the name Metashine MC1080RY by the company Toyal.

Finally, examples of nacres that may also be mentioned include polyethylene terephthalate flakes, notably those sold by the company Meadowbrook Inventions under the name Silver 1P 0.004×0.004 (silver flakes). Multilayer pigments based on synthetic substrates such as alumina, silica, calcium sodium borosilicate or calcium aluminum borosilicate, and aluminum, may also be envisaged.

The pigments with special effects may also be chosen from reflective particles, i.e. notably from particles of which the size, structure, notably the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, highlight points that are visible to the naked eye, i.e. more luminous points that contrast with their environment by appearing to sparkle.

The reflective particles may be selected so as not to significantly alter the coloring effect generated by the coloring agents with which they are combined, and more particularly so as to optimize this effect in terms of color rendition. They may more particularly have a yellow, pink, red, bronze, orange, brown, gold and/or coppery color or tint.

These particles may have varied forms and may notably be in platelet or globular form, in particular in spherical form.

Irrespective of their form, the reflective particles may or may not have a multilayer structure, and, in the case of a multilayer structure, may have, for example, at least one layer of uniform thickness, notably of a reflective material.

When the reflective particles do not have a multilayer structure, they may be composed, for example, of metal oxides, notably titanium or iron oxides obtained synthetically.

When the reflective particles have a multilayer structure, they may include, for example, a natural or synthetic substrate, notably a synthetic substrate at least partially coated with at least one layer of a reflective material, notably of at least one metal or metallic material. The substrate may be made of one or more organic and/or mineral materials.

More particularly, it may be chosen from glasses, ceramics, graphite, metal oxides, aluminas, silicas, silicates, notably aluminosilicates and borosilicates, synthetic mica, and mixtures thereof, this list not being limiting.

The reflective material may include a layer of metal or of a metallic material.

Reflective particles are notably described in JP-A-09188830, JP-A-10158450, JP-A-10158541, JP-A-07258460 and JP-A-05017710.

Still as an example of reflective particles including a mineral substrate coated with a layer of metal, mention may also be made of particles including a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the names Crystal Star GF 550 and GF 2525 by this same company.

Use may also be made of particles comprising a metallic substrate such as silver, aluminum, iron, chromium, nickel, molybdenum, gold, copper, zinc, tin, magnesium, steel, bronze or titanium, said substrate being coated with at least one layer of at least one metal oxide such as titanium oxide, aluminum oxide, iron oxide, cerium oxide, chromium oxide, silicon oxides, and mixtures thereof.

Examples that may be mentioned include aluminum powder, bronze powder or copper powder coated with $SiO_2$ sold under the name Visionaire by the company Eckart.

Mention may also be made of pigments with an interference effect which are not attached to a substrate, such as liquid crystals (Helicones HC from Wacker) or interference holographic glitter flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colors, and also particular optical effects such as metallic effects or interference effects.

The size of the pigment used in the composition according to the present invention is generally between 10 nm and 200 µm, preferably between 20 nm and 80 µm and more preferentially between 30 nm and 50 µm.

The pigments may be dispersed in the composition by means of a dispersant.

The dispersant serves to protect the dispersed particles against their agglomeration or flocculation. This dispersant may be a surfactant, an oligomer, a polymer or a mixture of several thereof, bearing one or more functionalities with a strong affinity for the surface of the particles to be dispersed. In particular, they may become physically or chemically attached to the surface of the pigments. These dispersants also contain at least one functional group that is compatible with or soluble in the continuous medium. In particular, notably 12-hydroxystearic acid esters and $C_8$ to $C_{20}$ fatty acid esters of polyols such as glycerol or diglycerol are used, such as poly(12-hydroxystearic acid) stearate with a molecular weight of approximately 750 g/mol, such as that sold under the name Solsperse 21 000 by the company Avecia, polyglyceryl-2 dipolyhydroxystearate (CTFA name) sold under the reference Dehymyls PGPH by the company Henkel, or polyhydroxystearic acid such as that sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the composition may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those that are described notably in Cosmetics and Toiletries, February 1990, Vol. 105, pages 53-64, before being dispersed in the composition in accordance with the invention. These organic agents may be chosen, for example, from waxes, for example carnauba wax and beeswax; fatty acids, fatty alcohols and derivatives thereof, such as stearic acid, hydroxystearic acid, stearyl alcohol, hydroxystearyl alcohol, lauric acid, and derivatives thereof; anionic surfactants; lecithins; sodium, potassium, magnesium, iron, titanium, zinc or aluminum salts of fatty acids, for example aluminum stearate or laurate; metal alkoxides; polyethylene; (meth)acrylic polymers, for example polymethyl methacrylates; polymers and copolymers containing acrylate units; alkanolamines; silicone compounds, for example silicones, in particular polydimethylsiloxanes; organofluorine compounds, for example perfluoroalkyl ethers; fluorosilicone compounds.

The surface-treated pigments that are useful in the composition may also have been treated with a mixture of these compounds and/or may have undergone several surface treatments.

The surface-treated pigments that are useful in the context of the present invention may be prepared according to surface-treatment techniques that are well known to those skilled in the art, or may be commercially available as is.

Preferably, the surface-treated pigments are coated with an organic layer.

The organic agent with which the pigments are treated may be deposited on the pigments by solvent evaporation, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is notably described in patent U.S. Pat. No. 4,578,266.

An organic agent covalently bonded to the pigments will preferably be used.

The agent for the surface treatment may represent from 0.1% to 50% by weight relative to the total weight of the surface-treated pigment, preferably from 0.5% to 30% by weight and even more preferentially from 1% to 20% by weight relative to the total weight of the surface-treated pigment.

Preferably, the surface treatments of the pigments are chosen from the following treatments:
    a PEG-silicone treatment, for instance the AQ surface treatment sold by LCW;
    a methicone treatment, for instance the SI surface treatment sold by LCW;
    a dimethicone treatment, for instance the Covasil 3.05 surface treatment sold by LCW;
    a dimethicone/trimethyl siloxysilicate treatment, for instance the Covasil 4.05 surface treatment sold by LCW;
    a magnesium myristate treatment, for instance the MM surface treatment sold by LCW;
    an aluminum dimyristate treatment, for instance the MI surface treatment sold by Miyoshi;
    a perfluoropolymethylisopropyl ether treatment, for instance the FHC surface treatment sold by LCW;
    an isostearyl sebacate treatment, for instance the HS surface treatment sold by Miyoshi;
    a perfluoroalkyl phosphate treatment, for instance the PF surface treatment sold by Daito;
    an acrylate/dimethicone copolymer and perfluoroalkyl phosphate treatment, for instance the FSA surface treatment sold by Daito;
    a polymethylhydrogen siloxane/perfluoroalkyl phosphate treatment, for instance the FS01 surface treatment sold by Daito;
    an acrylate/dimethicone copolymer treatment, for instance the ASC surface treatment sold by Daito;
    an isopropyl titanium triisostearate treatment, for instance the ITT surface treatment sold by Daito;
    an acrylate copolymer treatment, for instance the APD surface treatment sold by Daito;
    a perfluoroalkyl phosphate/isopropyl titanium triisostearate treatment, for instance the PF+ITT surface treatment sold by Daito.

According to a particular embodiment of the invention, the dispersant is present with organic or mineral pigments in submicron-sized particulate form in the dye composition.

The term "submicron" or "submicronic" is understood to mean pigments having a particle size that has been micronized by a micronization method and having a mean particle size of less than a micrometer (µm), in particular between 0.1 and 0.9 µm, and preferably between 0.2 and 0.6 µm.

According to one embodiment, the dispersant and the pigment(s) are present in an amount (dispersant:pigment) of between 1:4 and 4:1, particularly between 1.5:3.5 and 3.5:1 or better still between 1.75:3 and 3:1.

The dispersant(s) may therefore have a silicone backbone, such as silicone polyether and dispersants of amino silicone type other than the alkoxysilanes described previously. Among the suitable dispersants, mention may be made of:
- amino silicones, i.e. silicones comprising one or more amino groups such as those sold under the names and references: BYK LPX 21879 by BYK, GP-4, GP-6, GP-344, GP-851, GP-965, GP-967 and GP-988-1, sold by Genesee Polymers,
- silicone acrylates such as Tego® RC 902, Tego® RC 922, Tego® RC 1041, and Tego® RC 1043, sold by Evonik,
- polydimethylsiloxane (PDMS) silicones with carboxyl groups such as X-22162 and X-22370 by Shin-Etsu,
- epoxy silicones such as GP-29, GP-32, GP-502, GP-504, GP-514, GP-607, GP-682, and GP-695 by Genesee Polymers, or Tego® RC 1401, Tego® RC 1403, Tego® RC 1412 by Evonik.

According to a particular embodiment, the dispersant(s) are of amino silicone type other than the silicones described previously and are cationic.

Preferably, the pigment(s) is (are) chosen from mineral, mixed mineral-organic or organic pigments.

In one variant of the invention, the pigment(s) according to the invention are organic pigments, preferentially organic pigments surface-treated with an organic agent chosen from silicone compounds. In another variant of the invention, the pigment(s) according to the invention are mineral pigments.

The total amount of pigment(s) may range from 0.01% to 50% by weight, more particularly from 0.05% to 40% by weight and preferably from 0.1% to 35% by weight and preferably from 1% to 30%, relative to the total weight of the composition.

The composition of the invention may contain other colored or coloring species different from the pigments according to the invention, such as direct dyes or dye precursors.

The composition according to the invention may comprise water which may preferably be present in a content of less than 10% by weight, more preferentially less than 5% by weight relative to the weight of the composition.

More preferentially, the composition does not include water added during the preparation of the composition. The water possibly present may correspond to the residual water provided by the mixed ingredients.

Fatty Substance:

The composition according to the invention may also comprise one or more non-silicone fatty substances other than the fatty amines described previously, chosen from non-silicone fatty substances that are liquid at 25° C. and at atmospheric pressure or non-silicone fatty substances that are solid at 25° C. and at atmospheric pressure.

The non-silicone fatty substances that are liquid at 25° C. and at atmospheric pressure may be chosen from $C_6$-$C_{16}$ hydrocarbons or hydrocarbons containing more than 16 carbon atoms and in particular alkanes, oils of animal origin, oils of plant origin, glycerides or fluoro oils of synthetic origin, fatty alcohols, esters of a fatty acid and/or of a fatty alcohol, non-silicone waxes, and silicones.

The fatty alcohols that may be used in the cosmetic compositions of the invention may be saturated or unsaturated, and linear or branched, and include from 6 to 30 carbon atoms and more particularly from 8 to 30 carbon atoms. Examples that may be mentioned include cetyl alcohol, cetearyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

As regards the esters of a fatty acid and/or of fatty alcohols, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononate; isostearyl palmitate; methyl acetyl ricinoleate; myristyl stearate; octyl isononanoate; cetearyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

The solid non-silicone fatty substances according to the invention may be chosen from fatty alcohols, esters of a fatty acid and/or of a fatty alcohol, non-silicone waxes, ceramides, and mixtures thereof.

The term "solid fatty substance" is understood to mean a fatty substance that is solid at ambient temperature and at atmospheric pressure (25° C., 1 atm); they preferably have a viscosity of greater than 2 Pa·s, measured at 25° C. and at a shear rate of $1\ s^{-1}$.

The solid esters of a fatty acid and/or of a fatty alcohol that may be used are preferably chosen from esters resulting from a $C_9$-$C_{30}$ carboxylic fatty acid and/or from a $C_9$-$C_{30}$ fatty alcohol.

Preferably, the solid esters of a fatty acid and/or of a fatty alcohol are esters of a linear or branched, saturated carboxylic acid comprising at least 10 carbon atoms, preferably from 10 to 30 carbon atoms and more particularly from 12 to 24 carbon atoms, and esters of a linear or branched, saturated monoalcohol, comprising at least 10 carbon atoms, preferably from 10 to 30 carbon atoms and more particularly from 12 to 24 carbon atoms. The saturated carboxylic acids may be optionally hydroxylated, and are preferably monocarboxylic acids.

Esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxylated alcohols may also be used.

Mention may notably be made of octyldodecyl behenate, isocetyl behenate, cetyl lactate, stearyl octanoate, octyl octanoate, cetyl octanoate, decyl oleate, hexyl stearate, octyl stearate, myristyl stearate, cetyl stearate, stearyl stearate, octyl pelargonate, cetyl myristate, myristyl myristate, stearyl myristate, diethyl sebacate, diisopropyl sebacate, diisopropyl adipate, di-n-propyl adipate, dioctyl adipate, dioctyl maleate, octyl palmitate, myristyl palmitate, cetyl palmitate, stearyl palmitate, and mixtures thereof.

Preferably, the solid esters of a fatty acid and/or of a fatty alcohol are chosen from $C_9$-$C_{26}$ alkyl palmitates, in particular myristyl, cetyl or stearyl palmitate; $C_9$-$C_{26}$ alkyl myristates, such as cetyl myristate, stearyl myristate and myristyl myristate; $C_9$-$C_{26}$ alkyl stearates, in particular myristyl stearate, cetyl stearate and stearyl stearate; and mixtures thereof, even more preferentially cetyl palmitates.

When the composition comprises one or more non-silicone fatty substances, the total content of fatty substances may range from 0.01% to 20% by weight, preferably from 0.05% to 15% by weight, better still from 0.05% to 10% by weight relative to the total weight of the composition.

Additives:

The compositions may also contain at least one agent commonly used in cosmetics, for example chosen from reducing agents, organic solvents, softeners, antifoams, moisturizers, UV-screening agents, peptizers, solubilizers, fragrances, anionic, cationic, nonionic or amphoteric surfactants, proteins, vitamins, and mixtures thereof.

Surfactants:

The composition may comprise one or more nonionic surfactants.

They may be chosen from alcohols, α-diols and ($C_1$-$C_{20}$) alkylphenols, these compounds being polyethoxylated and/or polypropoxylated and/or polyglycerolated, the number of ethylene oxide and/or propylene oxide groups possibly ranging from 1 to 100, and the number of glycerol groups possibly ranging from 2 to 30; or alternatively these compounds comprising at least one fatty chain comprising from 8 to 30 carbon atoms and especially from 16 to 30 carbon atoms.

Mention may also be made of condensates of ethylene oxide and of propylene oxide with fatty alcohols; polyethoxylated fatty amides preferably containing from 2 to 30 ethylene oxide units, polyglycerolated fatty amides including on average from 1 to 5, and in particular from 1.5 to 4, glycerol groups; ethoxylated fatty acid esters of sorbitan preferably containing from 2 to 40 ethylene oxide units, fatty acid esters of sucrose, polyoxyalkylenated and preferably polyoxyethylenated fatty acid esters containing from 2 to 150 mol of ethylene oxide, including oxyethylenated plant oils, N—($C_{6-24}$ alkyl)glucamine derivatives, amine oxides such as ($C_{10-14}$ alkyl)amine oxides or N—($C_{10-14}$ acyl) aminopropylmorpholine oxides.

Mention may also be made of nonionic surfactants of alkyl(poly)glycoside type, represented notably by the following general formula:

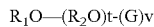

[Chem. 13]

wherein:

$R_1$ represents a linear or branched alkyl or alkenyl radical including 6 to 24 carbon atoms, notably 8 to 18 carbon atoms, or an alkylphenyl radical of which the linear or branched alkyl radical includes 6 to 24 carbon atoms, notably 8 to 18 carbon atoms, R2 represents an alkylene radical including 2 to 4 carbon atoms, G represents a sugar unit comprising 5 to 6 carbon atoms, t denotes a value ranging from 0 to 10, preferably from 0 to 4, v, the degree of polymerization, denotes a value ranging from 1 to 15, preferably from 1 to 4.

Preferably, the alkyl(poly)glycoside surfactants are compounds of the formula described above wherein:

$R_1$ denotes a linear or branched, saturated or unsaturated alkyl radical including from 8 to 18 carbon atoms, $R_2$ represents an alkylene radical including 2 to 4 carbon atoms, t denotes a value ranging from 0 to 3, preferably equal to 0, G denotes glucose, fructose or galactose, preferably glucose;

v, the degree of polymerization, denotes a value ranging from 1 to 15, preferably from 1 to 4; the average degree of polymerization being more particularly between 1 and 2.

The glucoside bonds between the sugar units are generally of 1-6 or 1-4 type, preferably of 1-4 type. Preferably, the alkyl(poly)glycoside surfactant is an alkyl(poly)glucoside surfactant. $C_8$/$C_{16}$-Alkyl(poly)glucosides 1,4, and in particular decyl glucosides and caprylyl/capryl glucosides, are most particularly preferred.

Among the commercial products, mention may be made of the products sold by the company Cognis under the names Plantaren® (600 CS/U, 1200 and 2000) or Plantacare® (818, 1200 and 2000); the products sold by the company SEPPIC under the names Oramix CG 110 and Oramix® NS 10; the products sold by the company BASF under the name Lutensol GD 70, or the products sold by the company Chem Y under the name AG10 LK.

Preferably, use is made of $C_8$/$C_{16}$-alkyl (poly)glycosides 1,4, in particular as an aqueous 53% solution, such as those sold by Cognis under the reference Plantacare® 818 UP.

The mono- or polyglycerolated surfactants preferably comprise an average number of glycerol groups ranging from 1 to 30, especially from 1 to 10, better still from 1.5 to 5. They preferably correspond to one of the following formulae:

[Chem. 14]

[Chem. 15]

or

[Chem. 16]

wherein:

R represents a saturated or unsaturated, linear or branched hydrocarbon-based (especially alkyl or alkenyl) radical including 8 to 40 carbon atoms, especially 10 to 30 carbon atoms, optionally comprising one or more heteroatoms such as O and N; and m is an integer ranging from 1 to 30, preferably from 1 to 10, better still from 1.5 to 6.

In particular, R may comprise one or more hydroxyl and/or ether and/or amide groups. Preferably, R is a mono- or polyhydroxylated $C_{10}$-$C_{20}$ alkyl or alkenyl radical.

Mention may be made of glyceryl stearate, sold, for example, by the company Gattefosse under the name Geleol®.

Mention may be made of polyglycerolated (3.5 mol) hydroxylauryl ether, such as the product Chimexane® NF from Chimex.

Mention may also be made of (poly)ethoxylated fatty alcohols preferably comprising one or more saturated or unsaturated, linear or branched hydrocarbon-based chains comprising 8 to 30 carbon atoms, preferably from 12 to 22 carbon atoms, optionally substituted with one or more hydroxyl (OH) groups, especially 1 to 4 hydroxyl groups.

When the chain is unsaturated, it may comprise one to three conjugated or non-conjugated carbon-carbon double bonds.

The (poly)ethoxylated fatty alcohols preferably correspond to formula (I):

[Chem. 17]

$$R_3-(OCH_2CH_2)cOH \quad (I)$$

wherein:
R$_3$ represents a linear or branched alkyl or alkenyl radical including from 8 to 40 carbon atoms, especially 8 to 30 carbon atoms, optionally substituted with one or more, especially 1 to 4, hydroxyl groups; and
c is an integer ranging from 1 to 200, in particular from 2 to 150, or even from 4 to 50 and even better still from 8 to 30.

The (poly)ethoxylated fatty alcohols are more particularly fatty alcohols comprising 8 to 22 carbon atoms, oxyethylenated with 1 to 30 mol of ethylene oxide (1 to 30 EO); mention may in particular be made of lauryl alcohol 2 EO; lauryl alcohol 3 EO; decyl alcohol 3 EO; decyl alcohol 5 EO and oleyl alcohol 20 EO.

Mention may also be made of (poly)ethoxylated plant oils such as the compounds of INCI name PEG-40 hydrogenated castor oil, PEG-60 hydrogenated castor oil.

The nonionic surfactants may advantageously be chosen from:
(i) the monoglycerolated or polyglycerolated surfactants as presented previously,
(ii) (poly)oxyalkylenated, in particular (poly)ethoxylated, fatty alcohols and in particular those of formula (I) wherein:
R$_3$ represents a linear or branched alkyl or alkenyl radical including from 8 to 40 carbon atoms, especially 8 to 30 carbon atoms, optionally substituted with one or more, especially 1 to 4, hydroxyl groups; and
c is an integer ranging from 1 to 200, in particular from 2 to 150, or even from 4 to 50 and even better still from 8 to 30;
(iii) (poly)oxyalkylenated (C$_8$-C$_{32}$)alkyl phenyl ethers, especially comprising 1 to 200, better still from 1 to 30, mol of ethylene oxide;
(iv) polyoxyalkylenated esters of C$_8$-C$_{32}$ fatty acids and of sorbitan, especially polyoxyethylenated esters of C$_8$-C$_{32}$ fatty acids and of sorbitan, preferably containing from 2 to 40 ethylene oxide units, better still from 2 to 20 ethylene oxide (EO) units; in particular polyoxyethylenated esters of C$_{10}$-C$_{24}$ fatty acids and of sorbitan, preferably containing from 2 to 40 ethylene oxide units, better still from 2 to 20 ethylene oxide (EO) units; and
(v) polyoxyethylenated esters of C$_8$-C$_{32}$ fatty acids, preferably containing from 2 to 150 ethylene oxide units; especially polyoxyethylenated esters of C$_{10}$-C$_{24}$ fatty acids, especially comprising 2 to 150 ethylene oxide (EO) units,
(vi) (poly)ethoxylated plant oils.

More preferentially, the nonionic surfactants may be chosen from:
(i) monoglycerolated or polyglycerolated surfactants,
(ii) (poly)oxyalkylenated, especially (poly)ethoxylated, fatty alcohols, and
(iii) (poly)ethoxylated plant oils.

Mention may in particular be made of:
glyceryl stearate;
(poly)ethoxylated lauryl alcohol, for instance the compounds of INCI name laureth-2, laureth-3, laureth-4, laureth-10, laureth-12, laureth-23, (poly)ethoxylated cetyl alcohol, for instance the compounds of INCI name ceteth-2, ceteth-10, (poly)ethoxylated stearyl alcohol, for instance the compounds of INCI name steareth-2, steareth-10, steareth-20, (poly)ethoxylated cetearyl alcohol, for instance the compounds of INCI name ceteareth-12, ceteareth-20, ceteareth-30, ceteareth-33, (poly)ethoxylated tridecyl alcohol, for instance the compound of INCI name trideceth-6, most particularly ceteareth-20 and ceteareth-12;
the compounds of INCI name PEG-40 hydrogenated castor oil, PEG-60 hydrogenated castor oil.

Preferably, the nonionic surfactants are chosen from glyceryl stearate, ceteareth-20, ceteareth-12, PEG-40 hydrogenated castor oil, and mixtures thereof.

Preferably, when they are present, the composition according to the invention comprises said nonionic surfactant(s) in an amount ranging from 0.01% to 10% by weight, even better still from 0.05% to 5% by weight, relative to the total weight of the composition.

Needless to say, those skilled in the art will take care to select this or these optional additives such that the advantageous properties intrinsically associated with the formation of the coating in accordance with the invention are not, or are not substantially, adversely affected.

Organic Solvents:
The composition according to the invention may comprise one or more organic solvents.

Examples of organic solvents that may be mentioned include lower C$_1$-C$_4$ alkanols, such as ethanol and isopropanol; polyols and polyol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, and mixtures thereof.

Preferably, the composition according to the invention comprises one or more organic solvents chosen from C$_1$-C$_4$ lower alkanols, more preferentially ethanol.

When they are present, the organic solvents are present in a total content preferably inclusively between 0.1% and 80% by weight approximately relative to the total weight of the composition a) and more preferentially between 1% and 70% by weight approximately and even more particularly inclusively between 2% and 60% by weight relative to the total weight of the composition a).

Device:
The aerosol device comprises at least one pressurized container comprising at least one propellant b).

The propellant(s) b) may or may not be present in the composition a) as previously described.

The container of the device according to the invention can have rigid walls and can directly contain the composition a).

As a variant, the container can have rigid walls and can contain a flexible-walled bag which contains the composition a).

According to this configuration, the composition a) in the bag may not comprise propellant b), the latter being in the volume defined between the rigid walls of the container and the bag.

Preferably, the composition a) contained in the bag itself also comprises at least one propellant b).

The device comprises a means which makes it possible to deliver the compositions, the means comprising at least one dispensing valve which surmounts the container.

The valve is in selective fluidic communication with the inside of the container via a valve inlet orifice, the communication being established in response to the activating of an activation means, such as a push-button.

When the device comprises a rigid-walled container which contains a flexible bag, the valve is then equipped with two inlet orifices, one of the orifices being able to communicate with the inside of the bag and the other being able to communicate with the volume defined between the bag and the rigid walls of the container.

When the container does not contain a bag, it is equipped with a dip tube which makes it possible to convey the composition to the inlet orifice of the dispensing valve.

When the container contains a bag, the inlet orifice of the valve opens into the bag.

The device can comprise at least one diffuser which caps the valve. The push-button may be part of the diffuser.

The diffuser may be equipped with one or more dispensing pipes provided to convey the composition(s) up to one or more dispensing orifices.

Documents U.S. Pat. Nos. 3,917,121, 4,720,046 and WO 00/76880 disclose examples of devices.

The diffuser may comprise a single outlet orifice and diffusion branches that radiate from said orifice. As a variant, the diffuser comprises a plurality of outlet orifices. Advantageously, the outlet orifices may be arranged so as to obtain a diffusion grille.

Preferably, the pressurized container of the device according to the invention has rigid walls and directly contains the composition a).

Preferably, the composition a) comprises one or more propellants b).

It should be noted that in the context of the invention, the propellant(s) can be used to allow the expulsion of the composition(s).

The propellant(s) are present in the pressurized container according to the invention preferably in a total content ranging from 1% to 99% by weight, more preferentially from 10% to 98% by weight, better still from 40% to 97% by weight, even better still from 70% to 96% by weight relative to the total weight of the composition (packaged in the aerosol device). When the propellant(s) are present in the composition a), the total weight of the composition corresponds to the total weight of the composition a). When the propellant(s) are not present in the composition a), the total weight of the composition corresponds to the weight of the composition a)+the weight of the propellant(s).

Preferably, the propellant(s) are present in the pressurized container according to the invention in a total amount ranging from 1% to 99% by weight, more preferentially from 10% to 98% by weight, better still from 40% to 97% by weight, even better still from 70% to 96% by weight, relative to the total weight of the composition a).

The propellant(s) is (are) in particular chosen from air, hydrocarbon-based gases, inert gases, and mixtures thereof. Mention may be made in particular of hydrocarbon-based gases, for instance propane, n-butane, isobutane, and mixtures thereof; fluoro gases, for instance chlorodifluoromethane, dichlorodifluoromethane, difluoroethane, chlorodifluoroethane, dichlorotetrafluoroethane, etc., and mixtures thereof, hydrofluorocarbon-based gases; dimethyl ether and mixtures of dimethyl ether with one or more hydrocarbon-based gases; nitrogen, air and carbon dioxide, and mixtures thereof may also be used as inert propellant gases in the present invention.

Preferably, the propellant(s) is (are) chosen from hydrocarbon-based gases containing from 2 to 6 carbon atoms, more preferentially isobutane, propane, n-butane, dimethyl ether, and mixtures thereof, more preferentially dimethyl ether.

More preferentially, the device according to the invention comprises dimethyl ether.

According to another preferred embodiment, the propellant is a mixture of dimethyl ether and hydrofluorocarbon-based gases.

When the propellant(s) are present in the composition a), the total amount of copolymer(s) of crotonic acid or crotonic acid derivative may range from 0.05% to 5% by weight relative to the weight of the composition, preferably from 0.1% to 2% by weight relative to the weight of the composition, preferably from 0.1% to 1% by weight relative to the total weight of the composition a).

When the propellant(s) are present in the composition a), the fatty amine(s) is (are) present in a total amount which may range from 0.001% to 2%, preferably from 0.005% to 1%, better still from 0.01% to 0.5% by weight relative to the weight relative to the total weight of the composition a).

When the propellant(s) are present in the composition a), the silicone(s) may be present in a total amount which may range from 0.01% to 3% by weight relative to the total weight of the composition, preferably from 0.05% to 1%, more preferentially from 0.05% to 0.5%, by weight relative to the total weight of the composition a).

When the propellant(s) are present in the composition a), the total amount of pigment(s) may range from 0.01% to 10% by weight, more particularly from 0.05% to 5% by weight and preferably from 0.1% to 3% by weight and preferably from 0.5% to 2% by weight relative to the total weight of the composition a).

The gases are pressurized, more particularly at least partially pressurized in liquid form.

Advantageously, the dye composition which is delivered from the pressurized container is in liquid form.

Process:

Another subject of the invention is a process for dyeing keratin fibers such as the hair, comprising the application to said fibers of a composition delivered from a device as defined above, optionally followed by drying.

The composition delivered by the aerosol device described above may be used on wet or dry keratin fibers, and also on any type of fair or dark, natural or dyed, permanent-waved, bleached or relaxed fibers.

According to a particular embodiment of the process of the invention, the fibers are washed before applying the composition described above.

By virtue of the device according to the invention, the application is uniform on the whole of the head of hair.

The dyeing process is generally performed at ambient temperature (between 15 and 25° C.).

After the application of the composition, the fibers may be left to dry or may be dried, for example at a temperature of greater than or equal to 30° C. According to a particular embodiment, this temperature is greater than 40° C. According to a particular embodiment, this temperature is greater than 45° C. and less than 220° C.

The drying, if it is employed, can be carried out immediately after application or after a leave-on time which can range from 1 minute to 30 minutes.

Preferably, if the fibers are dried, they are dried, in addition to a supply of heat, with a flow of air. This flow of air during drying makes it possible to improve the strand separation of the coating.

During drying, a mechanical action may be exerted on the locks, such as combing, brushing or running the fingers through. This operation may similarly be performed once the fibers have been dried, naturally or otherwise.

The drying step of the process of the invention may be performed with a hood, a hairdryer, a straightening iron, a climazone, etc.

When the drying step is performed with a hood or a hairdryer, the drying temperature is between 40 and 110° C., preferably between 50 and 90° C.

When the drying step is performed with a straightening iron, the drying temperature is between 110 and 220° C., preferably between 140 and 200° C.

The present invention will now be described more specifically by means of examples, which do not in any way limit the scope of the invention. However, the examples make it possible to support specific features, variants and preferred embodiments of the invention.

EXAMPLE

Compositions (g/100 g) AM: Active Material

TABLE 1

| Composition | A |
| --- | --- |
| VA/crotonates/vinyl neodecanoate copolymer | 5.2 |
| Amodimethicone (and) Trideceth-10 (and) Acetic acid (Belsil ADM 6102E from Wacker) | 5.1 (1.8 AM of amodimethicone) |
| Dimethicone (Xiameter PMX-200 Silicone Fluid from Dow Corning) | 1.6 |
| Stearamidopropyl dimethylamine (Lexamine S-13 from Inolex Chemical Company) | 1.8 |
| CI 77499 (and) CI 77492 (and) CI 77491 (and) CI 77891 (and) Triethoxycaprylylsilane (Light Brown Blend from Sensient) | 25 |
| Cetearyl isononanoate/ceteareth-12/ceteareth-20/glyceryl stearate mixture (Emulgade CM from BASF) | 3 |
| Filler | qs |
| PEG-40 hydrogenated castor oil | 1.5 |
| Ethanol | qs |

Composition A will be applied to keratin fibers in three different ways:
with an aerosol device according to the invention,
with a comparative device of pump bottle type, and
with the fingers (without device).

Aerosol Device According to the Invention:
Composition A is packaged in an aerosol device with dimethyl ether, in propellant/fluid proportions of 95/5.

The aerosol device according to the invention comprises a DMPR154 diffuser of the Cosmos Minijet brand, a 40×100 12 bar container of the Ogival brand and a push-in valve of the S90 Precision Europe brand with a nozzle diameter of 4.0 mm, a nozzle orifice of 0.41 mm, a PGA orifice of 0.33 mm and a valve body orifice of 0.46 mm).

The aerosol device according to the invention is actuated and the mixture is delivered in liquid form. 3 g of the mixture (that is to say 0.15 g of composition A) are applied to a 1 g lock of natural hair containing 90% gray hairs.

Comparative Device of Pump Bottle Type:
Composition A alone is packaged in a comparative device of pump bottle type. The comparative device comprises a transparent 100 ml PET bottle (GL20/410 Tall of the Boston Roun° brand, a PZ1/HV/150 pump of the Aptar brand and a DV30 20 nozzle of the Aptar brand.

The comparative device is actuated and composition A is delivered in liquid form. 0.15 g of composition A is applied to a 1 g lock of natural hair containing 90% gray hairs.

With the Fingers:
0.15 g of composition A is applied with the finger to a 1 g lock of natural hair containing 90% gray hairs.

The locks dyed with the aerosol device according to the invention, with the comparative device and with the finger are then combed, dried with a hairdryer and then combed again.

Results:
The results in terms of cosmetic feel, product distribution along the locks and color uniformity were evaluated on dried locks, by 5 experts, in a blind test.

TABLE 2

| Type of application | Aerosol device (invention) | Pump bottle device (comparative) | With the finger (comparative) |
| --- | --- | --- | --- |
| Cosmetic feel | Soft, natural feel, good hair strand separation | Rough feel | Sticky feel, poor hair strand separation |
| Product distribution along the locks | homogeneous | Heterogeneous | Heterogeneous |
| Color | Color uniformity | Color heterogeneity | Color heterogeneity |

Thus, unlike the application with the comparative device or the application with the finger, the application of the composition to the locks of hair using the aerosol device according to the invention is rapid, easy and uniform.

Furthermore, the aerosol device according to the invention makes it possible to obtain locks of hair with good hair strand separation which have a pleasant cosmetic feel, in particular good softness, manageability and an absence of tack. Furthermore, the color obtained on the locks of hair is uniform.

The invention claimed is:

1. An aerosol device comprising:
at least one pressurized container comprising:
a) at least one composition comprising:
(i) at least one copolymer resulting from the polymerization of at least one crotonic acid monomer or crotonic acid derivative and of at least one vinyl ester monomer,
(ii) at least one fatty amine chosen from fatty amidoamines having the formula (L) below:

$$RCON(H)R''N(R)_2 \quad (L)$$

wherein R represents a monovalent hydrocarbon-based radical containing from 5 to 29 carbon atoms;
wherein R″, which is independently chosen from a divalent hydrocarbon-based radical containing less than 6 carbon atoms; and
wherein R′, which is independently chosen from a linear or branched, saturated or unsaturated and substituted or unsubstituted monovalent hydrocarbon-based radical containing less than 6 carbon atoms, and
(iii) at least one mineral pigment, wherein the total amount of mineral pigment(s) ranges from 1% to 50% by weight relative to the total weight of the composition,
b) at least one propellant, and
a means configured to deliver the composition.

2. The device of claim 1, wherein the at least one copolymer results from the polymerization of at least one crotonic acid monomer and of at least one vinyl ester monomer.

3. The device of claim 1, wherein the at least one crotonic acid derivative is chosen from crotonic acid esters or amides.

4. The device of claim 1, wherein the at least one crotonic acid derivative is chosen from crotonic acid esters of formula $CH_3CH=CHCOOR'_1$ with $R'_1$ independently chosen from a linear, branched or cyclic, saturated or unsaturated, carbon-based chain, containing 1 to 30 carbon atoms, optionally comprising one or more functions chosen from —OH, —OR' with R' being $C_1$-$C_6$ alkyl.

5. The device of claim 1, wherein the at least one crotonic acid derivative is chosen from the crotonic acid amides of formula $CH_3CH=CHCONR'_2R''_2$ with $R'_2$ and $R''_2$ independently chosen from hydrogen or a linear, branched or cyclic, saturated or unsaturated, optionally aromatic, carbon-based chain, containing 1 to 30 carbon atoms, optionally comprising one or more functions chosen from —OH, —OR' with R' being $C_1$-$C_6$ alkyl.

6. The device of claim 1, wherein the at least one copolymer results from the polymerization of at least one crotonic acid monomer or crotonic acid derivative and of at least two different vinyl ester monomers.

7. The device of claim 1, wherein the at least one vinyl ester monomer is chosen from vinyl acetate, vinyl propionate, vinyl butyrate (or butanoate), vinyl ethylhexanoate, vinyl neononanoate, vinyl neododecanoate, vinyl neodecanoate, vinyl pivalate, vinyl cyclohexanoate, vinyl benzoate, vinyl 4-tert-butylbenzoate, vinyl trifluoroacetate, or mixtures thereof.

8. The device of claim 1, wherein the at least one copolymer is chosen from copolymers resulting from the polymerization of crotonic acid, vinyl acetate and vinyl propionate, copolymers resulting from the polymerization of crotonic acid, vinyl acetate and vinyl neodecanoate, or mixtures thereof.

9. The device of claim 1, wherein at least one copolymer is a crotonic acid/vinyl acetate/vinyl neodecanoate terpolymer.

10. The device of claim 2, wherein the at least one copolymer further comprises other monomers comprising allylic or methallylic esters or vinyl ethers.

11. The device of claim 1, wherein the at least one crotonic acid copolymer resulting from the polymerization of at least one crotonic acid monomer or crotonic acid derivative and of at least one vinyl ester monomer is present in an amount ranging from 0.05% to 15% by weight, relative to the weight of the composition.

12. The device of claim 1, wherein the at least one fatty amine is chosen from tertiary fatty amines.

13. The device of claim 1, wherein the at least one fatty amine is stearamidopropyl dimethylamine.

14. The device of claim 1, wherein the at least one fatty amine is present in a total amount ranging from 0.001% to 10% by weight, relative to the total weight of the composition.

15. The device of claim 1, wherein the composition further comprises at least one silicone.

16. The device of claim 15, wherein the composition comprises at least one non-amino silicone and/or at least one amino silicone.

17. The device of claim 16, wherein the composition comprises at least one non-amino silicone chosen from the non-amino silicones with the INCI name dimethicone and/or at least one amino silicone with the INCI name amodimethicone.

18. The device of claim 15, wherein the at least one silicone is present in a total amount which ranges from 0.01% to 10% by weight, relative to the total weight of the composition.

19. The device of claim 1, wherein the container has rigid walls and directly contains the composition.

20. The device of claim 1, wherein the at least one propellant is chosen from hydrocarbon-based gases containing from 2 to 6 carbon atoms.

21. A process for dyeing keratin fibers, comprising the application to the keratin fibers of a composition delivered from a device, optionally followed by drying, wherein the device comprises:
at least one pressurized container comprising:
  a) at least one composition comprising:
    (i) at least one copolymer resulting from the polymerization of at least one crotonic acid monomer or crotonic acid derivative and of at least one vinyl ester monomer,
    (ii) at least one fatty amine chosen from fatty amidoamines having the formula (L) below:

$$RCON(HR)R''N(R')_2 \qquad (L)$$

wherein R represents a monovalent hydrocarbon-based radical containing from 5 to 29 carbon atoms;
    wherein R", which is independently chosen from a divalent hydrocarbon-based radical containing less than 6 carbon atoms; and
    wherein R', which is independently chosen from a linear or branched, saturated or unsaturated and substituted or unsubstituted monovalent hydrocarbon-based radical containing less than 6 carbon atoms, and
    (iii) at least one mineral pigment wherein the total amount of mineral pigment(s) ranges from 1% to 50% by weight relative to the total weight of the composition,
  b) at least one propellant, and
a means configured to deliver the composition.

* * * * *

UNITED STATES PATENT AND TRADEMARK OFFICE
CERTIFICATE OF CORRECTION

PATENT NO. : 12,161,746 B2
APPLICATION NO. : 17/784378
DATED : December 10, 2024
INVENTOR(S) : Malayphone Sananikone et al.

Page 1 of 1

It is certified that error appears in the above-identified patent and that said Letters Patent is hereby corrected as shown below:

In the Claims

Claim 1, Column 30, Line 44, change "RCON(H)R"N(R)2" to -- RCON(H)R"N(R')2 --

Signed and Sealed this
Twenty-fifth Day of March, 2025

Coke Morgan Stewart
*Acting Director of the United States Patent and Trademark Office*